United States Patent
Narimatsu et al.

[11] Patent Number: 5,467,771
[45] Date of Patent: Nov. 21, 1995

[54] PULSE WAVE SENSOR

[75] Inventors: Kiyoyuki Narimatsu, Kasugai; Norio Kawamura, Nagoya, both of Japan

[73] Assignee: Colin Corporation, Japan

[21] Appl. No.: 307,445

[22] Filed: Sep. 19, 1994

[30] Foreign Application Priority Data

Oct. 26, 1993 [JP] Japan ............... 5-267173

[51] Int. Cl.$^6$ ................................ A61B 5/00
[52] U.S. Cl. .................. 128/672; 128/687; 128/690
[58] Field of Search .................. 128/672, 687–690, 128/677

[56] References Cited

U.S. PATENT DOCUMENTS

| | | | |
|---|---|---|---|
| 5,101,829 | 4/1992 | Fujikawa | 128/672 |
| 5,131,400 | 7/1992 | Harada et al. | 128/690 |
| 5,179,956 | 1/1993 | Harada et al. | 128/672 |
| 5,238,000 | 8/1993 | Niwa | 128/672 |

FOREIGN PATENT DOCUMENTS 4-67839  3/1992  Japan .

OTHER PUBLICATIONS

Polyurethanes—The Bridge between silicone rubber and plastics. no date available.

*Primary Examiner*—Angela D. Sykes
*Assistant Examiner*—Robert L. Nasser, Jr
*Attorney, Agent, or Firm*—Oliff & Berridge

[57] ABSTRACT

A pressure pulse wave sensor for detecting a pressure pulse wave produced from an arterial vessel of a living subject in synchronism with heartbeat of the subject, the sensor having a press surface adapted to be pressed on a body surface of the subject, a protruding portion protruding from the press surface and having a top surface, and at least one pressure sensing element provided in the top surface of the protruding portion, for detecting the pressure pulse wave produced from the arterial vessel, the top surface of the protruding portion being covered with a resilient protective layer, the pulse wave sensor further comprising a hard member which surrounds the protruding portion such that a top end of the hard member is substantially flush with the resilient protective layer covering the top surface of the protruding portion.

7 Claims, 5 Drawing Sheets

PRESSURE SENSING ELEMENT NOs. 0-29

PULSE WAVE SENSOR

BACKGROUND OF THE INVENTION

1. Field of the Invention

The present invention relates to a pulse wave sensor adapted to be pressed on a body surface of a living subject for detecting a pressure pulse wave produced from an artery of the subject.

2. Discussion of the Related Art

There is known a pulse wave sensor having a press surface adapted to be pressed on a body surface of a living subject, a protruding portion protruding from the press surface, and sensing means provided in a top surface of the protruding portion, for detecting a pressure pulse wave produced from an artery of the subject. As disclosed in U.S. Pat. No. 5,179,956 assigned to the Assignee of the present application and Laid-open Publication No. 4-67839 of unexamined Japanese Patent Application, the pulse wave sensor as described above has a resilient protective layer formed of an epoxy resin, silicone resin or silicone rubber. More specifically described, the resilient protective layer covers the press surface of the protruding portion adapted to be pressed on the body surface and additionally forms inclined surfaces between the protruding portion and a protection plate, which surfaces are inclined from the press surface of the protruding portion toward the protection plate. This resilient protective layer is provided for the purpose of protecting one or more pressure sensing elements provided in the top surface of the protruding portion and a cable connected thereto, as well as mitigating pain as felt by the subject when the edges and/or corners of the protruding portion are pressed on a skin (i.e., body surface) of the subject for detecting the pulse wave. In measuring blood pressure of the subject by using this pulse wave sensor, the protruding portion of the pulse wave sensor is pressed on the body surface over an artery such as a radial artery from which the pulse wave is detected, such that the artery partially becomes flattened. As a result, pressure transmitted from the artery is detected by the pressure sensing elements of the pulse wave sensor.

In many cases, however, hard bone and tendon are present near the artery from which the pressure pulse wave is to be detected. When the pulse wave sensor is pressed on the body surface with a pressing force necessary to measure the blood pressure, the resilient protective layer which surrounds the protruding portion receives relatively large pressure from the bone and tendon, and tensile force caused by friction between the protruding portion of the pulse wave sensor and the skin of the subject on which the pulse wave sensor is pressed. The pressure from the bone and tendon and the tensile force, each received by the resilient protecting layer, are undesirably transmitted to the top surface of the protruding portion covered with the resilient protective layer, and consequently adversely increase the pressure detected by the pressure sensing element. Therefore, the blood pressure detected by the pulse wave sensor as described above inevitably includes an erroneous component which results from the above pressure and tensile force. Thus, the above-described conventional pulse wave sensor is not capable of assuring accurate measurement of the blood pressure.

SUMMARY OF THE INVENTION

The present invention has been developed in the light of the above situation. It is therefore an object of the present invention to provide a pressure pulse wave sensor which is capable of detecting a pressure pulse wave from an artery of a living subject without being adversely influenced by the pressure transmitted from a bone and a tendon located near the artery.

The above object may be attained according to the present invention which provides a pressure pulse wave sensor for detecting a pressure pulse wave produced from an arterial vessel of a living subject in synchronism with heartbeat of the subject, the sensor having a press surface adapted to be pressed on a body surface of the subject, a protruding portion protruding from the press surface and having a top surface, and at least one pressure sensing element provided in the top surface of the protruding portion, for detecting the pressure pulse wave produced from the arterial vessel, the top surface of the protruding portion being covered with a resilient protective layer, wherein the improvement comprises a hard member which surrounds the protruding portion such that a top end of the hard member is substantially flush with the resilient protective layer covering the top surface of the protruding portion.

In the pressure pulse wave sensor constructed according to the present invention, the hard member surrounds the protruding portion whose top surface is covered with the resilient protective layer, so that the resilient protective layer does not extend over the top end of the hard member. When the pressure pulse wave sensor is pressed on the body surface over the artery for, e.g., measuring the blood pressure of the subject, the high pressure from the bone and tendon near the artery acting on the pulse wave sensor and the tensile force caused by friction between the sensor and the skin of the subject are received solely by the hard member which surrounds the protruding portion and which is not likely to be deformed by these pressure and tensile force. Thus, the resilient protective layer provided on the top surface of the protruding portion is free from such pressure and tensile force. Accordingly, the pulse wave sensor constructed according to the present invention is capable of reducing influence of the pressure from the bone and tendon near the artery from which the pressure pulse wave is detected, to thereby assure accurate measurement of the blood pressure.

BRIEF DESCRIPTION OF THE DRAWINGS

The above and other objects, features and advantages of the present invention will be better understood by reading the following detailed description of the presently preferred embodiments of the invention when considered in connection with the accompanying drawings, in which.

DETAILED DESCRIPTION OF THE PREFERRED EMBODIMENTS

Figure 1:
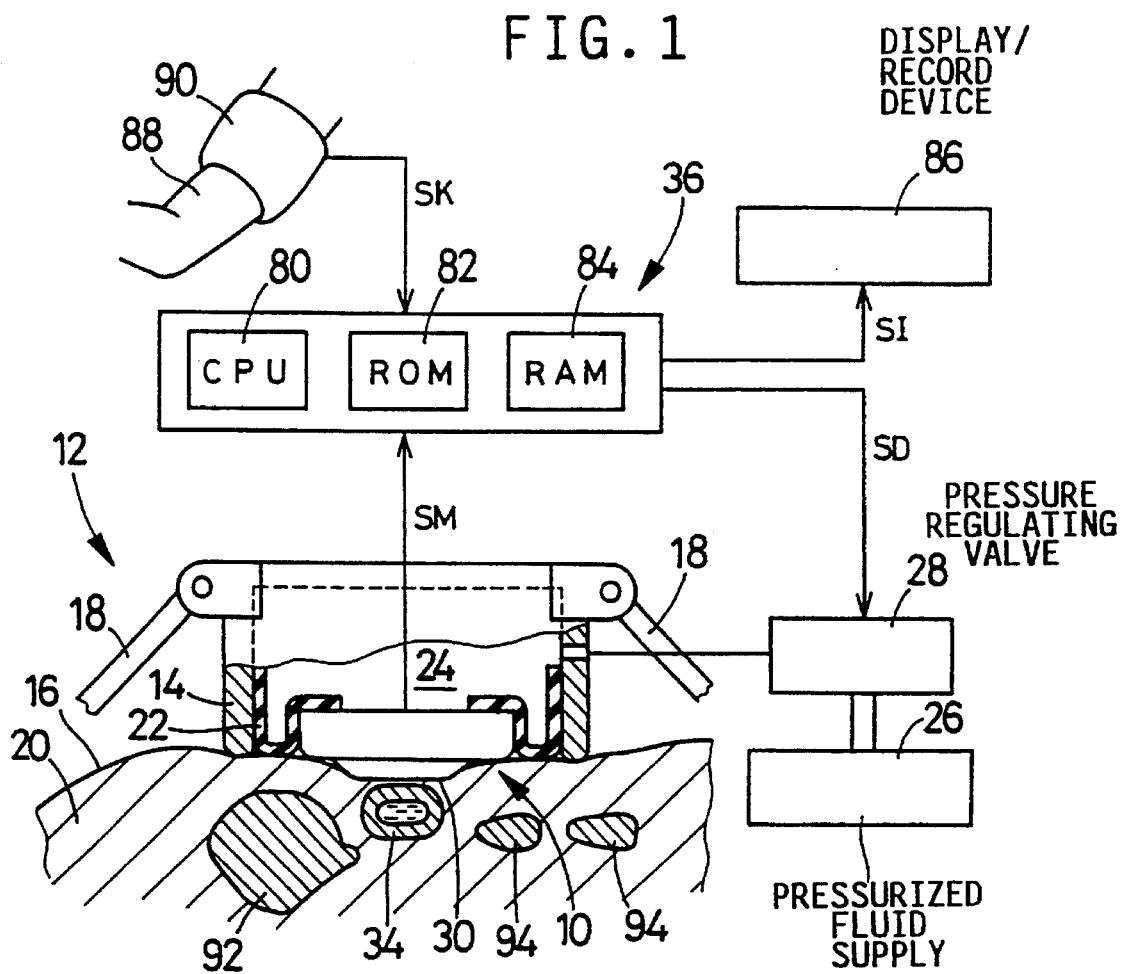
FIG. 1 is a diagrammatic view showing a pressure pulse wave detecting apparatus which includes a pressure pulse wave sensor constructed according to the present invention.

Referring to FIG. 1, there is shown a pulse wave detecting apparatus 12 which includes a pressure pulse wave sensor 10 constructed according to a first embodiment of the present invention. In the figure, reference numeral 14 denotes a housing which is open at one of axially opposite ends thereof. The housing 14 is set on a wrist 20 of a living subject by means of wrist bands 18, 18, such that an open end of the housing 14 is opposed to a body surface (i.e., skin) 16 of the subject. In the housing 14, there are provided a flexible diaphragm 22 which is secured to an inner wall surface of the housing 14 and a pressure pulse wave sensor 10 which is secured to the diaphragm 22. The pulse wave sensor 10 is disposed within the housing 14 such that the sensor 10 is displaceable relative to the housing 14 and that the sensor 10 is advanceable out of the opening of the housing 14. The housing 14, diaphragm 22 and pulse wave sensor 10 cooperate with each other to define a pressure chamber 24. The pressure chamber 24 is adapted to receive pressurized fluid, such as pressurized air, from a pressurized fluid supply 26 via a pressure regulating valve 28. Thus, the pressure pulse wave sensor 10 is pressed against the body surface 16 with a suitable pressing force corresponding to the pressure in the pressure chamber 24.

Figure 2:
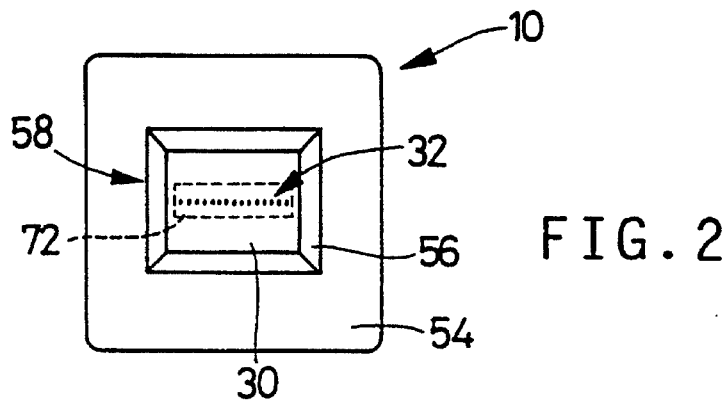
FIG. 2 is a plan view of the pressure pulse wave sensor of FIG. 1 as seen from the side of a top surface thereof.

As shown in FIG. 2, the pressure pulse wave sensor 10 is constituted by a semiconductor chip formed of a monocrystalline silicon, for instance, and a multiplicity of pressure sensing elements 32 such as pressure sensing diodes (thirty pressure sensing diodes, for instance), which elements 32 are arranged in a row in a top surface 30 of the semiconductor chip. The pressure pulse wave sensor 10 is adapted to be pressed against a radial artery 34 via the body surface 16, such that the row of the pressure sensing elements 32 substantially perpendicularly intersects the radial artery 34. In this situation, each pressure sensing element 32 detects an oscillatory pressure wave, that is, pressure pulse wave transmitted from the radial artery 34 to the body surface 16. It is noted that each interval between adjacent pressure sensing elements 32 in the row is made sufficiently small to such an extent that a predetermined necessary and sufficient number of the pressure sensing elements 32 can be located over the radial artery 34. In addition, a length of the row of the pressure sensing elements 32 is predetermined such that the length is sufficiently larger than a diameter of the radial artery 34. Each of the pressure sensing elements 32 outputs an electric signal, namely, a pulse wave signal SM representative of the detected pressure pulse wave, and the produced pulse wave signal SM is received by a control device 36.

Figure 3:
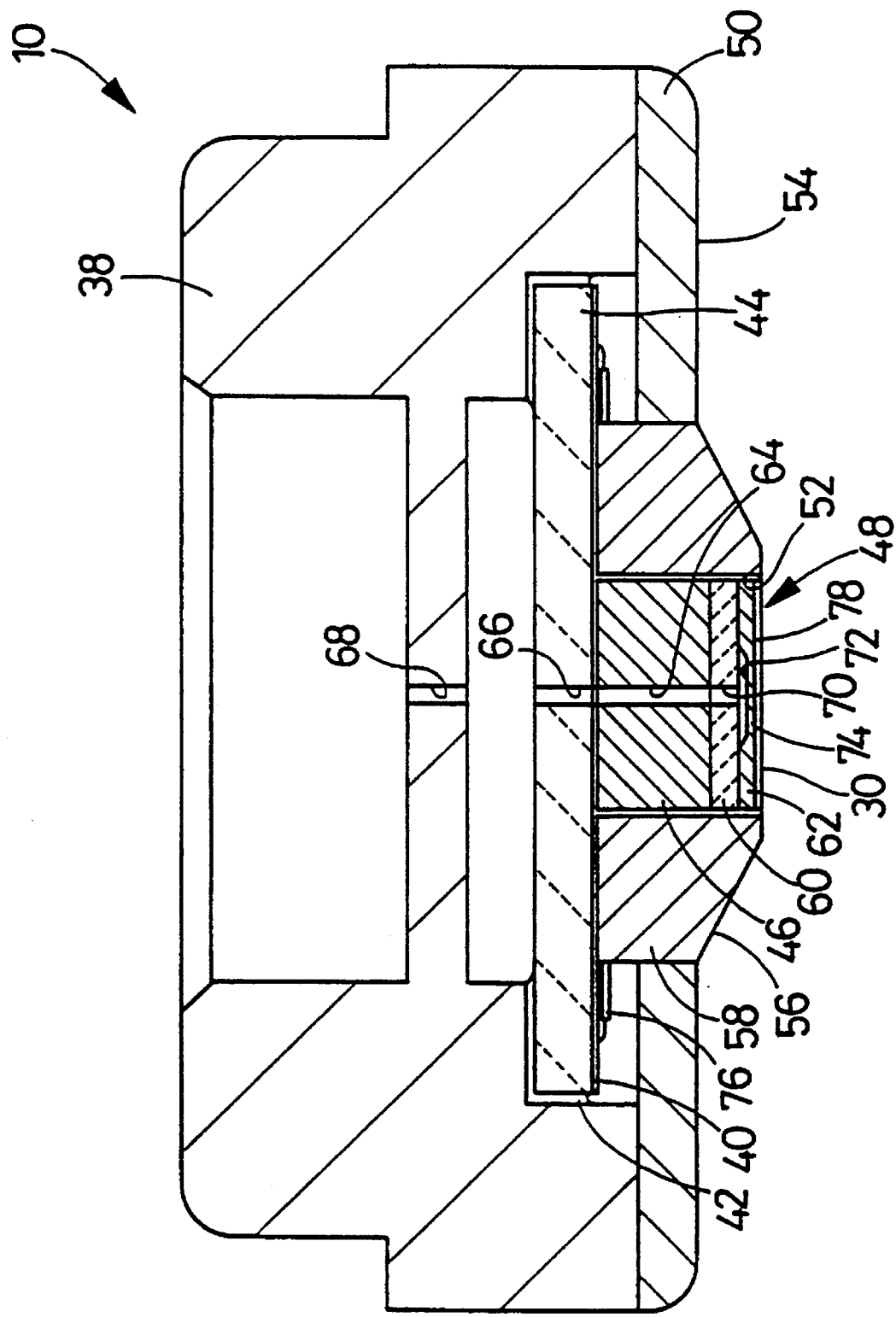
FIG. 3 is a cross-sectional view of the pressure pulse wave sensor of FIG. 1.

As shown in FIG. 3, the pressure pulse wave sensor 10 includes a sensor head case 38, plate member 44, spacer member 46, sensor chip 48, protection plate 50 and a stadium 58. The sensor head case 38 is formed of plastics, for example, and is fixed to a central portion of the diaphragm 22. The plate member 44 is formed of a ceramic, for example, and is fixed within a central recess of the head case 38 at one of opposite surfaces thereof via an adhesive layer 42. The other surface of the plate member 44 is covered with a circuit film 40. The spacer member 46 assumes a rectangular parallelopiped shape and is secured to a central portion of the plate member 44. The sensor chip 48 is attached to the spacer member 46 by a suitable adhesive. The protection plate 50 is formed of a metal, and is adhered to the head case 38 for protecting the circuit film 40 and connector pads connecting between the circuit film 40 and a flexible flat cable 76 described later.

Figure 4:
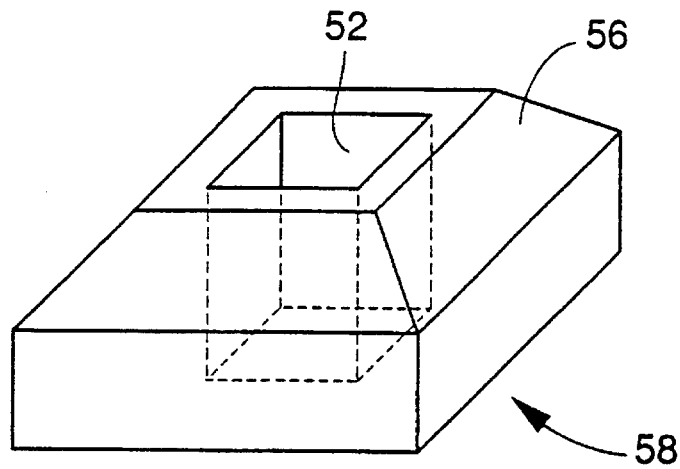
FIG. 4 is a perspective view showing a stadium as a hard member employed in the pressure pulse wave sensor of FIG. 1.

As shown in FIG. 4, the stadium 58 assumes a generally rectangular configuration. The stadium 58 is formed of, for example, a ceramic or a hard resin, and is secured to the above-indicated other surface of the plate member 44 which is covered with the circuit film 40, so that the stadium 58 is disposed in a space defined by the protective plate 50 and the spacer member 46 to which the sensor chip 48 is secured. The stadium 58 has a square hole 52 formed through the thickness thereof for accommodating the spacer member 46 and the sensor chip 46 secured thereto, and has a large wall thickness. The stadium 58 further has tapered surfaces 56 which are tapered from a press surface 54 of the protection plate 50 toward a top end of the stadium 58 at a predetermined angle. The spacer member 46 is formed of aluminum and surface-treated with an electrical insulating material such as plastics or alumite, so that the spacer member 46 serves as an electrical insulator. The plate member 44 whose surface on the side of the stadium 58 is covered with the circuit film 40 functions as a junction circuit for electrically connecting the sensor chip 48 and the control device 36. The junction circuit may include a multiplexer, pre-amplifier, regulator and other active elements, as needed. The plate member 44 also functions as a member for mechanically supporting the sensor chip 48. In the present embodiment, the spacer member 46 and sensor chip 48 cooperate with each other to constitute a protruding portion, while the stadium 58 constitutes a hard member. The tapered surfaces 56 of the stadium 58 are provided for the purpose of preventing the living subject on which the pulse wave detecting apparatus 12 is worn, from feeling pain which would be caused by contact of the edges and/or corners of the top surface 30 of the protruding portion with the body surface of the subject.

The sensor chip 48 includes a back-up plate 60 formed of a glass having a high rigidity and a semiconductor chip 62 formed of a monocrystalline-silicon plate and adhered to one of opposite surfaces of the back-up plate 60 remote from the spacer member 46. The back-up plate 60 which serves as a spacer member has a through-hole 70 formed through the thickness thereof for introducing atmospheric pressure to a back surface of the semiconductor chip 62 on the side of the back-up plate 60 via central holes 64, 66, 68 formed through the spacer member 46, plate member 44 and head case 38, respectively. The semiconductor chip 62 has a thickness of about 300 μm, and an elongate recess 72 formed in the back surface thereof so as to provide an elongate small-thickness portion 74 having a thickness ranging from about several microns to several tens of microns. The pressure sensing elements 32 are formed on this small-thickness portion 74 by a well-known semiconductor producing method such as diffusion or injection of impurities. The circuit film 40 which covers one of opposite surfaces of the plate member 44 on the side of the stadium 58 is electrically connected to the pressure sensing elements 32 by the flexible flat cable 76 which is provided in a recess (not shown) of the stadium 58. More specifically described, the flat cable 76 is bent in the recess of the stadium 58 such that the cable 76 extends from the circuit film 40 toward the sensing elements 32 along the surface of the plate member 44 and side surfaces of the spacer member 46. In FIG. 3, only end portions of the flat cable 76 on the side of the circuit film 40 are shown, which end portions are connected to the circuit film 40 on the plate member 44. One of opposite surfaces of the semiconductor chip 62 remote from the spacer member 46 is covered with a resilient protective layer 78 formed of silicone rubber for protecting the pressure sensing elements 32. In this arrangement, a top surface of this resilient protective layer 78 is substantially flush with a top end of the stadium 58 (i.e., the lowermost surface of the stadium 58 as seen in FIG. 3).

Figure 5:
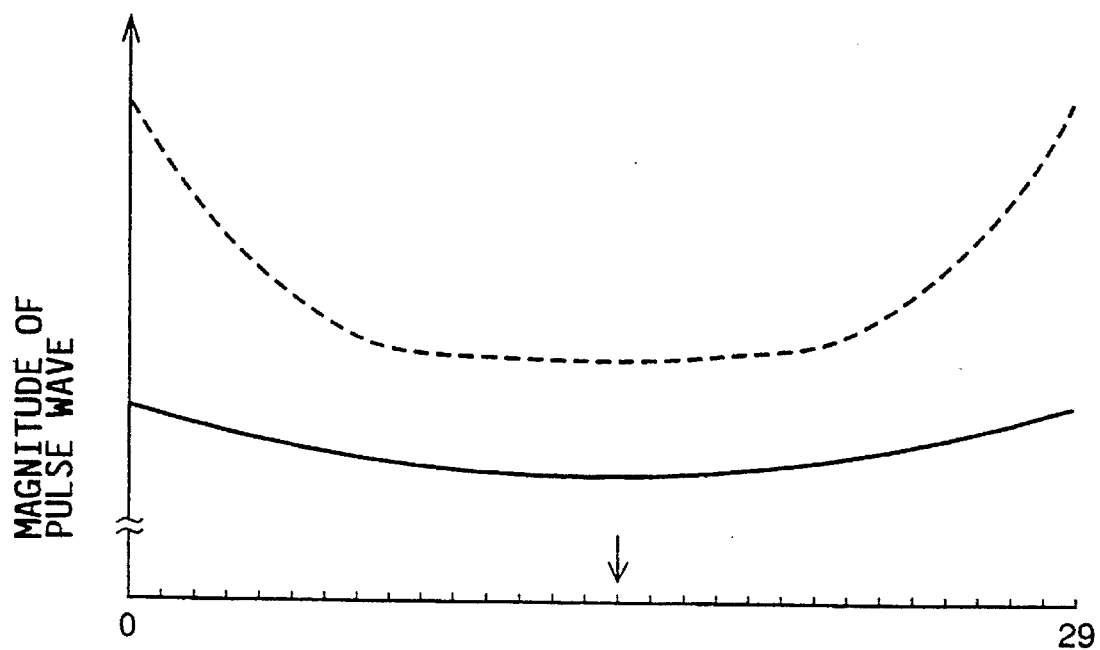
FIG. 5 is a graph illustrating a tonogram curve obtained by plotting minimum magnitudes of pulse waves detected by respective pressure sensing elements of the pressure pulse wave sensor of FIG. 1.

Referring back to FIG. 1, the control device 36 includes a microcomputer which is constituted by a central processing unit (CPU) 80, a read-only memory (ROM) 82, a random-access memory (RAM) 84, and other components. The CPU 80 processes input signals according to programs pre-stored in the ROM 82 while utilizing the temporary-storage function of the RAM 84, and determines an optimum pressing force by which the pulse wave sensor 10 is pressed on the body surface of the living subject and an optimum pressure sensing element 32a selected among all of the sensing elements 32, on the basis of the pulse wave signals SM received from each of the pressure sensing elements 32 during a pressure-increase period in which the pressure of the pressure chamber 24 is increased, according to known algorithms. The control device 36 supplies a pressure-regulating signal SD to the pressure regulating valve 28, to thereby adjust the pressure within the pressure chamber 24 for maintaining the determined optimum pressing force, and reads in the pulse wave signal SM supplied from the determined optimum pressure sensing element 32a to thereby continuously detect the pressure pulse wave. The control device 36 generates an output signal SI representative of the detected pulse wave and supplies the signal SI to a display/record device 86 so as to display and record the detected pulse wave. With the pulse wave sensor 10 pressed over the radial artery 34 via the body surface 16 by the optimum pressing force determined as described above, minimum magnitudes (i.e., lower-peak magnitudes) of the pulse wave signals SM produced by the respective pressure sensing elements 32 are plotted in a direction of the row of the sensing elements 32 to thereby provide a tonogram curve as shown in FIG. 5. Further, the control device 36 determines whether a pressing condition of the pulse wave sensor 10 with respect to the body surface 16 remains appropriate or not, on the basis of a chronological change in successive tonogram curves. If it is judged that the pressing condition of the pulse wave sensor 10 is changed due to physical motion of the subject, for example, and therefore, the current pressing condition is no longer appropriate for pressing the body surface, the control device 36 adjusts the current value of the optimum pressing force to a suitable value, and maintains the newly determined pressing force. The control device 36 is connected to an inflatable cuff 90 which is wound around an upper arm 88 of the subject and which generates a blood pressure signal SK. The above-described pulse wave signal SM generated by the optimum pressure sensing element 32a is subjected to so-called "calibration" based on the blood pressure signal SK, so that the signal SM accurately represents the blood pressure of the living subject. In the pressure chamber 24, there is provided a pressure sensor (not shown) for detecting the pressure in the chamber 24. This pressure sensor generates a pressure signal representative of the pressure within the pressure chamber 24 and supplies this signal to the control device 36. In FIG. 1, reference numerals 92, 94 respectively designate a radial bone and a tendon.

Next, there will be described the operation of the pulse wave detecting apparatus 12 constructed as described above.

When an ON/OFF switch (not shown) is set to an "ON" position, the regulating valve 28 is controlled so as to supply the pressurized fluid from the fluid supply 26 to the pressure chamber 24, so that the pressure in the chamber 24 is increased at a constant low rate to a predetermined value, for example, about 250 mmHg. During this slow pressure increase period, the control device 36 reads in the pulse wave signals SM generated by each pressure sensing element 32 of the pulse wave sensor 10 as well as the pressure signal representative of the pressure in the pressure chamber 24. Then, the control device 36 calculates an amplitude of each of the pulse waves which are represented by the pulse wave signals SM generated by each pressure sensing element 32. It is noted that the amplitude of each pulse wave is represented by a difference between a maximum (an upper peak) and a minimum (a lower peak) magnitude of each pulse wave. The control device 36 selects, as an optimum pressure sensing element 32a, one of the pressure sensing elements 32 which detected a pulse wave having a maximum amplitude. The maximum amplitude is the greatest amplitude of all the amplitudes of the pulse waves detected by each of the pressure sensing elements 32. The control device 36 further determines, as an optimum pressing force, a pressing force of the pulse wave sensor 10 at which the optimum pressure sensing element 32a has detected the pulse wave having the maximum amplitude. Subsequently, with the pulse wave sensor 10 being pressed with the thus determined optimum pressing force, the optimum pressure sensing element 32a continuously detects a pulse wave and supply the pulse wave signal SM representative of the detected pulse wave to the control device 36. The control device 36 stores the received signal SM and then, supplies a display/record signal SI representative of the detected pulse wave to the display/record device 86 so as to display and record the pulse wave detected by the optimum pressure sensing element 32a. When a predetermined number of pulse waves (e.g. 8 pulse waves) are detected with the pressing force of the pulse wave sensor 10 maintained at the above-indicated optimum level, the control device 36 determines an average minimum magnitude of the detected pulse waves for each of the pressure sensing elements 32. A solid line in the graph of FIG. 5 shows a tonogram curve obtained by plotting the respective average minimum magnitudes of the detected pulse waves for the pressure sensing elements 32. In the graph of FIG. 5, the pressure sensing element indicated by an arrow represents the optimum pressure sensing element 32a as described above.

For detection of the pressure pulse waves produced from the artery, the pressure pulse wave sensor 10 is pressed against the radial artery 34 via the body surface 16 of the subject. In this situation, the pulse wave sensor 10 may receive, in a diagonal direction, a pressure from the radial bone 92 or tendon 94 located adjacent to the radial artery 34. In the case of a conventional pressure pulse wave sensor wherein tapered surfaces are integrally formed with a resilient protective layer covering a top surface of a protruding portion to protect an outer surface of a semiconductor chip, the tapered surfaces undesirably receive the pressure from the bone and tendon and tensile force caused by friction between the tapered surfaces and the body surface (skin) 16 since the tapered surfaces of the conventional pulse wave sensor are formed of silicone rubber and therefore, liable to act like fluid upon receiving the above-indicated pressure and tensile force. As a result, the pressure is transmitted to the resilient protective layer covering the top surface of the protruding portion, and pressure sensing elements 32 undesirably detect this pressure as a part of the pressure pulse wave generated from the radial artery 34. In the graph of FIG. 5, a tonogram curve obtained by the conventional pulse wave sensor is indicated by a broken line. As can be understood from this tonogram curve, the magnitudes of the pulse waves detected by the conventional pulse wave sensor do not accurately represent the magnitudes of the pulse waves generated from the radial artery 34, but are increased by the amount corresponding to the above-indicated pressure applied from the bone and tendon. In particular, the pressure sensing elements located adjacent to the tapered surfaces (the sensing elements Nos. 0 and 29) detect considerably large magnitudes of the pulse waves. In this case, the detected pulse wave signals SM must be compensated by the amount corresponding to the pressure from the bone and tendon. However, calculation or estimation of the amount to be used for the compensation requires technically difficult process, making it difficult to accurately obtain the blood pressure. On the other hand, the pulse wave sensor 10 constructed according to the present embodiment of the invention has the stadium 58 which is formed of a ceramic or a hard resin having a high rigidity and which surrounds the side surfaces of the protruding portion whose top surface 30 is covered with the resilient protective layer 78. In this arrangement, only the tapered surfaces 56 of the stadium 58 receive the above-described pressure from the bone and tendon in the diagonal direction. Further, since the stadium 58 made of a ceramic or a hard resin is not likely to be deformed, the pressure received by the tapered surfaces 56 is not transmitted to the pressure sensing elements 32 provided on the semiconductor chip 62 of the protruding portion. Thus, the present pulse wave sensor 10 provides the tonogram curve indicated by the solid line in the graph of FIG. 5 which accurately represents the pulse waves generated from the radial artery 34. Accordingly, the pulse waves detected by the present pulse wave sensor 10 are free from the conventionally required compensation of the detected pulse waves as described above, permitting the pressure pulse wave detecting apparatus 12 to obtain the blood pressure of the living subject with high accuracy.

According to the present embodiment, even if the pressure from the radial bone 92, tendon 94, or body surface (skin) 16 acting on the pulse wave sensor 10 is changed due to physical motion of the living subject during the detection of the pressure pulse wave, the change in the pressure does not influence the detection by the pressure sensing elements 32 since the pressure is received only by the tapered surfaces 56 of the stadium 58 and is not transmitted to the pressure sensing elements 32. Therefore, in the present arrangement wherein the pulse wave signal SM is calibrated by utilizing the blood pressure signal SK obtained from the cuff 90, the calibration does not occur with a slight physical motion of the subject during the detection of the pressure pulse wave, whereby the continuous operation of the pressure pulse wave detecting apparatus 12 for measuring the blood pressure is not interrupted by the calibration effected by using the cuff 90.

The pressure pulse wave detecting apparatus 12 using the present pulse wave sensor 10 is capable of obtaining the blood pressure of the living subject with improved accuracy, and does not suffer from an adverse variation of the pulse wave signal SM resulting from a slight physical motion of the subject during the pulse wave detection. In this respect, the pulse wave detecting apparatus 12 using the present pulse wave sensor 10 may eliminate the provision of the cuff 90 which was conventionally used in combination with the pressure pulse detecting apparatus 12 to effect the calibration of the pulse wave signal SM, thereby reducing discomfort of the subject caused by attachment of the cuff 90 to the upper arm 88 during the blood pressure detection.

Figure 6:
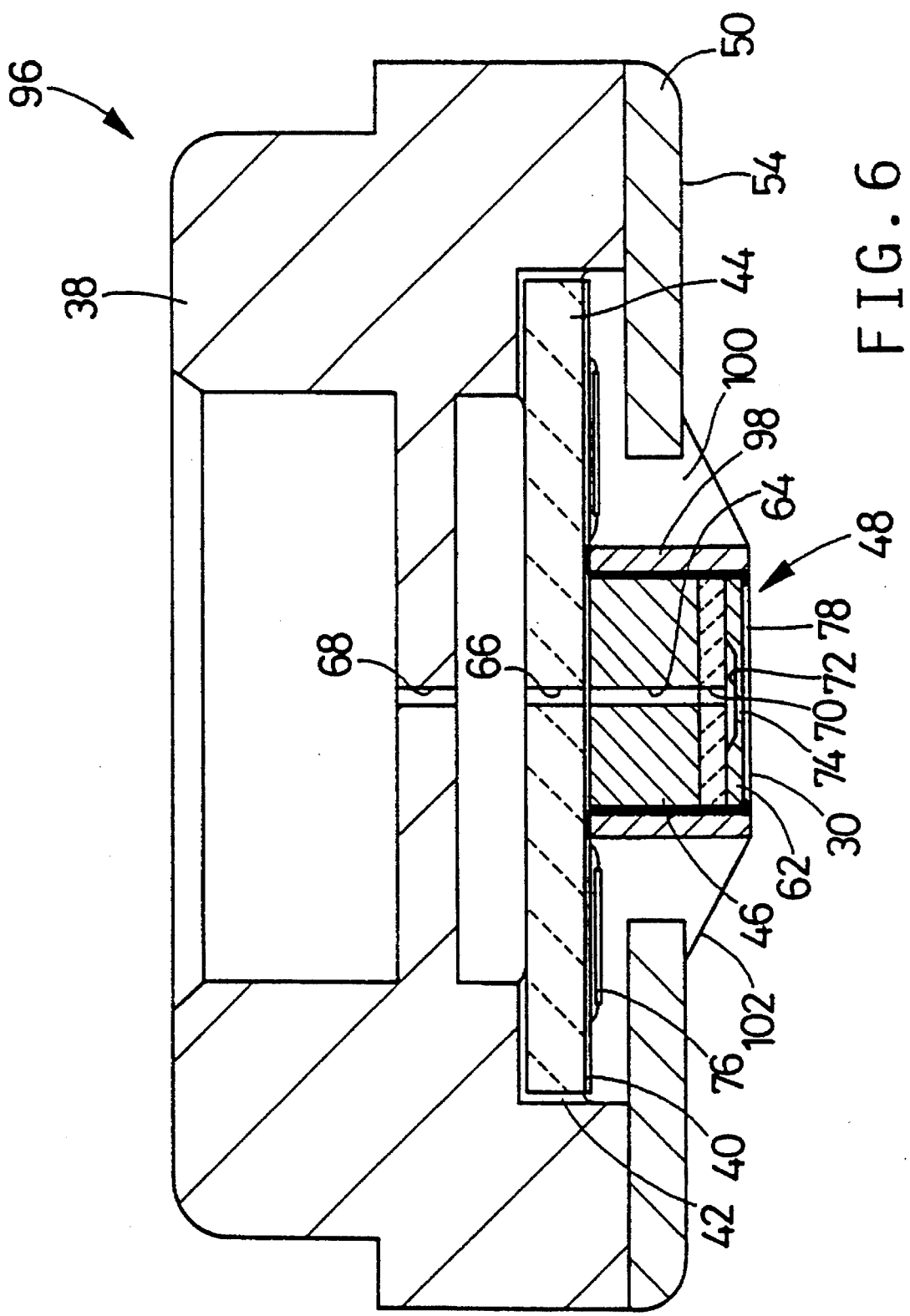
FIG. 6 is a cross-sectional view corresponding to FIG. 3, showing a pressure pulse wave sensor constructed according to another embodiment of the present invention.

Referring next to FIG. 6, there is shown a pressure pulse wave sensor 96 according to a second embodiment of the present invention. Since this pulse wave sensor 96 is substantially identical in construction with the pulse wave sensor 10 of the preceding embodiment, the same reference numerals as used in the preceding embodiment are used to identify the corresponding components, and detailed description of which is not provided.

Figure 7:
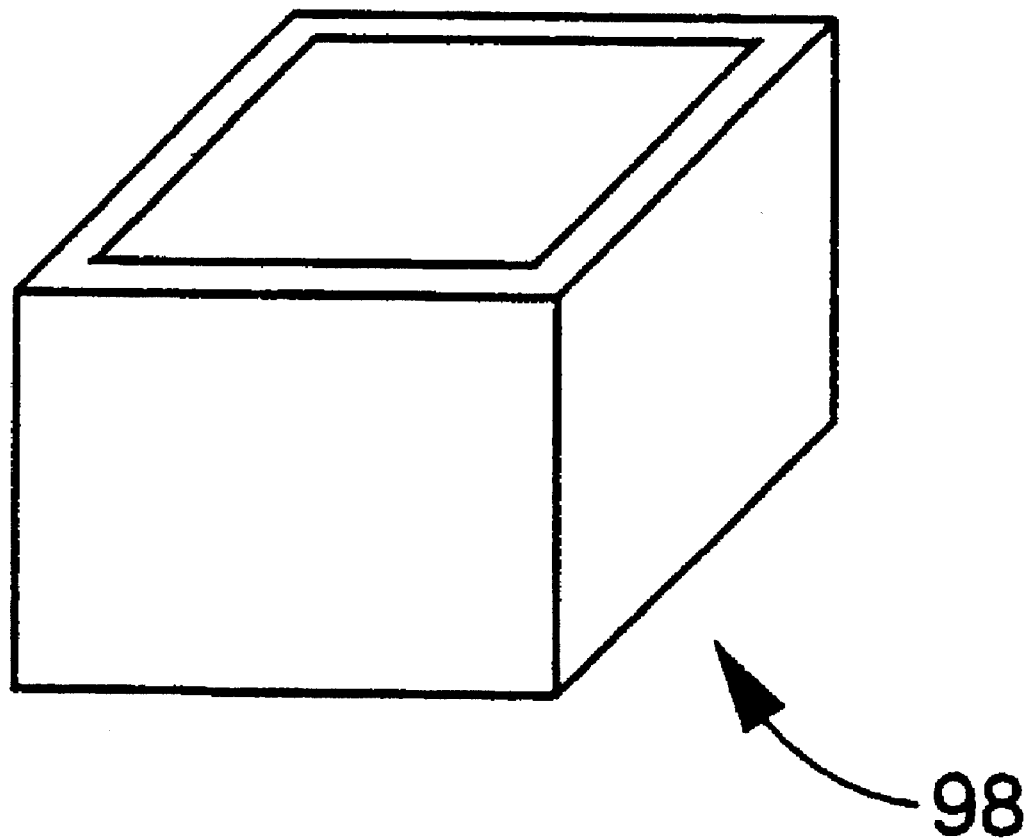
FIG. 7 is a perspective view showing a shut-out member as a hard member employed in the pressure pulse wave sensor of FIG. 6.

The pulse wave sensor 96 of this embodiment has a rectangular shut-out member 98 in place of the stadium 58 of the preceding embodiment, as shown in FIG. 7. The shut-out member 98 is secured at one of opposite ends thereof to one of opposite surfaces of the plate member 44 which surface is on the side of the spacer member 46 and sensor chip 48, so that shut-out member 98 surrounds the side surfaces of the protruding portion constituted by the spacer member 46 and sensor chip 48. Like the stadium 58, the shut-out member 98 is formed of a ceramic or a hard resin, for instance. A space defined by the protection plate 50 and the shut-out member 98 is filled with silicone rubber 100, and tapered surfaces 102 similar to the tapered surfaces 56 of the stadium 58 are formed between the top end of the shut-out member 98 and the protection member 50. The top surface 30 of the protruding portion is covered with the resilient protective layer 78 formed of silicone rubber. In this modified embodiment, too, the shut-out member 98 formed of a ceramic or a hard resin having a high rigidity surrounds the side surfaces of the protruding portion which includes the resilient protective layer 78 provided to cover the top surface 30 of the protruding portion. The silicone rubber 100 having the tapered surfaces 102 and the resilient protective layer 78 covering the top surface 30 of the protruding portion are separate from each other by the shut-out member 98. In this arrangement, the pressure from the radial bone 92 or tendon 94 in the diagonal direction, and tensile force caused by friction between the body surface (skin) 16 and the pulse wave sensor 96 are received only by the tapered surfaces 102. Even when the silicone rubber 100 is deformed by the pressure, the shut-out member 98 interposed between the silicone rubber 100 and the protruding portion prevents the pressure from being transmitted to the resilient protection layer 78. Accordingly, the present pulse wave sensor 96 is capable of detecting the pressure pulse wave which is free from the influence of the radial bone 92 and tendon 94, to thereby assure accurate blood pressure measurement. It is noted that the shut-out member 98 serves as a hard member in the present embodiment.

While the present invention has been described in detail in its presently preferred embodiments, it is to be understood that the present invention may otherwise be embodied.

Although in the illustrated embodiments the semiconductor chip 62 has in a top surface thereof a plurality of pressure sensing elements 32 for detecting the pressure pulse wave of the living subject, it is possible to detect the pressure pulse wave by using a single pressure sensing element 32.

While the stadium 58 and protection plate 50 are formed of respective independent members in the first embodiment, the stadium 58 may be integrally formed with the protection plate 50 to constitute a single member.

The stadium 58 or shut-out member 98 as a hard member may be provided in abutting contact with the side surfaces of the protruding portion constituted by the spacer member 46 and the sensor chip 48. Alternatively, a slight clearance may be formed between the side surfaces of the protruding portion and an inner surface of the stadium 58 or shut-out member 98. Furthermore, the hard member in the form of the stadium 58 or shut-out member 98 may be formed of a glass, for example. In any case, the advantages offered by the principle of the present invention can be attained by the pulse wave sensor 10, 96 wherein only the tapered surfaces 56, 102 are adapted to receive the pressure in the diagonal direction from the bone or tendon located near the artery from which the pulse wave is detected, and wherein the hard member prevents the pressure from being transmitted to the resilient protective layer 78 which covers the top surface of the sensor chip 48.

Although the cuff 90 is employed in combination with the pulse wave sensor 10, 96 in the pressure pulse wave detecting apparatus 12 in the above embodiments, it is possible to detect the pressure pulse wave solely by the detecting apparatus 12 to which the present pulse wave sensor 10 is applied.

It is to be understood that the present invention may be embodied with other changes, improvements and modifications which may occur to those skilled in the art without departing from the scope of the invention defined in the following claims.

What is claimed is:

1. A pressure pulse wave sensor for detecting a pressure pulse wave produced from an arterial vessel of a living subject in synchronism with a heartbeat of the subject comprising:

a press surface adapted to be pressed on a body surface of the subject;

a protruding portion protruding from said press surface and having a top surface, said top surface of said protruding portion being covered with a resilient protective layer, which is formed of a first material;

at least one pressure sensing element provided in said top surface of said protruding portion for detecting said pressure pulse wave produced from said arterial vessel; and a hard member which surrounds said protruding portion such that a top end of said hard member is substantially flush with said resilient protective layer covering said top surface of said protruding portion, said hard member being formed of a second material which is different from said first material and having a hardness higher than that of said resilient protective layer.

2. A pressure pulse wave sensor according to claim 1, wherein said hard member has a hole formed through a thickness thereof for accommodating said protruding portion.

3. A pressure pulse wave sensor according to claim 1, wherein said second material of said hard member is selected from the group consisting of a ceramic, a hard resin and a glass.

4. A pressure pulse wave sensor according to claim 1, wherein said hard member has tapered surfaces which are tapered from said press surface toward said top end of said hard member at a predetermined angle.

5. A pressure pulse wave sensor according to claim 1 further comprising: a plate member providing said press surface, said hard member cooperating with said plate member to define a space therebetween; and a rubber member filling said space, said rubber member having tapered surfaces with respect to said press surface, so that said resilient protective layer covering said top surface of said protruding portion is separate from said rubber member by said hard member interposed therebetween.

6. A pressure pulse wave sensor according to claim 1, wherein said at least one pressure sensing element comprises a plurality of pressure sensing elements formed in said top surface of said protruding portion so as to be arranged in a row.

7. A pressure pulse wave sensor according to claim 1, wherein said first material of said resilient protective layer is a rubber.

* * * * *